(12) United States Patent
Ochoco et al.

(10) Patent No.: US 8,351,628 B2
(45) Date of Patent: Jan. 8, 2013

(54) SIGNAL PROCESSING FOR COCHLEAR IMPLANTS

(75) Inventors: Jomar G. Ochoco, St. Paul, MN (US); Peter J. Schiller, Coon Rapids, MN (US)

(73) Assignee: Envoy Medical Corporation, St. Paul, MN (US)

( * ) Notice: Subject to any disclaimer, the term of this patent is extended or adjusted under 35 U.S.C. 154(b) by 761 days.

(21) Appl. No.: 12/411,212

(22) Filed: Mar. 25, 2009

(65) Prior Publication Data

US 2010/0246872 A1 Sep. 30, 2010

(51) Int. Cl.
H04R 25/00 (2006.01)
(52) U.S. Cl. .......................... 381/328; 381/314; 381/316
(58) Field of Classification Search .................. 381/312, 381/314, 316, 328
See application file for complete search history.

(56) References Cited

U.S. PATENT DOCUMENTS

| | | | |
|---|---|---|---|
| 4,419,995 A | 12/1983 | Hochmair et al. | |
| 4,495,384 A | 1/1985 | Scott et al. | |
| 4,499,339 A | 2/1985 | Richard | |
| 4,617,536 A | 10/1986 | Richard | |
| 5,035,242 A | 7/1991 | Franklin et al. | |
| 5,047,994 A | 9/1991 | Lenhardt et al. | |
| 5,451,900 A | 9/1995 | Haga et al. | |
| 5,571,148 A | 11/1996 | Loeb et al. | |
| 5,741,314 A | 4/1998 | Daly et al. | |
| 5,800,475 A | 9/1998 | Jules | |
| 5,874,981 A | 2/1999 | Haas et al. | |
| 6,073,050 A | 6/2000 | Griffith | |
| 6,217,508 B1 | 4/2001 | Ball et al. | |
| 6,377,693 B1 | 4/2002 | Lippa et al. | |
| 7,266,209 B1 | 9/2007 | House | |
| 7,286,675 B1 | 10/2007 | O'Neill et al. | |
| 2006/0184213 A1 | 8/2006 | Griffith | |
| 2008/0195177 A1 | 8/2008 | Ibrahim | |
| 2008/0253594 A1* | 10/2008 | Rasmussen et al. | 381/312 |
| 2010/0034409 A1* | 2/2010 | Fay et al. | 381/326 |

OTHER PUBLICATIONS

House, D.D.S., M.D., William F., "Cochlear Implants: My Perspective," http://www.allhearcom/art_my_intro.php, accessed Mar. 19, 2009. (51 pgs.).
House, D.D.S., M.D., William F., "The AllHear Cochlear Implant System: the AllHear Devices, their Manufacture, Preliminary Test Results, & the Future," http://www.allhear.com/art_sys_intro.php, accessed Mar. 19, 2009. (49 pgs.).
Med-El Corporation, "Complete Cochlear Cover With Med-Els Deep Insertion Electrode," http://www.medel.com/US/img/download/20872_CompCochCov.pdf, accessed Mar. 19, 2009. (12 pgs.).
Med-El Corporation, "Focus on FineHearing Technology," http://www.medel.com/US/img/download/20712US_r10—FocusOn_FineHearing.pdf, accessed Mar. 19, 2009. (8 pgs.).

* cited by examiner

Primary Examiner — Matthew E Warren
(74) Attorney, Agent, or Firm — Brooks, Cameron & Huebsch, PLLC

(57) ABSTRACT

The present disclosure includes methods, devices, and systems for cochlear implants. One method embodiment for cochlear implant signal processing includes processing a differential analog audio signal using amplitude modulation and pulse-width modulation. The method includes driving a transmission coil on an external unit of the cochlear implant with the pulse-width and amplitude modulated signal. The method also includes driving a reception coil on an internal unit of the cochlear implant with an output of the transmission coil.

16 Claims, 14 Drawing Sheets

SIGNAL PROCESSING FOR COCHLEAR IMPLANTS

TECHNICAL FIELD

The present disclosure relates generally to cochlear implant devices, methods, and systems, and more particularly, to signal processing for cochlear implants.

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

External components may include a microphone, a processor, and a transmitter. Cochlear implants may detect sounds via an ear level microphone that conveys these sounds to a wearable processor. Some processors may be worn behind the patient's ear. An electronic signal from the processor may be sent to a transmission coil worn externally behind the ear over the implant. The transmission coil may send a signal to the implant receiver, located under the patient's scalp.

Internal components may include a receiver and one or more electrodes. Some cochlear implants may include additional processing circuitry among the internal components. The receiver may direct signals to one or more electrodes that have been implanted within the cochlea. The responses to these signals may then be conveyed along the auditory nerve to the cortex of the brain where they are interpreted as sound.

Some cochlear implants may be fully implanted and include a mechanism for measuring sound similar to a microphone, signal processing electronics, and means for directing signals to one or more electrodes implanted within the cochlea. Fully implanted cochlear implants typically do not include a transmission coil or a receiver coil.

Some sound processing units may be specially fitted for their users, e.g., by audiologists specially trained in programming such devices. Programming sound processors involves measurement of the patient's sensitivity to the electronic impulses. Other sound quality such as pitch also may be assessed. These responses are used to customize each patient's implant system so that sound is as clear and comfortable as possible for the patient.

DETAILED DESCRIPTION

Figure 1:
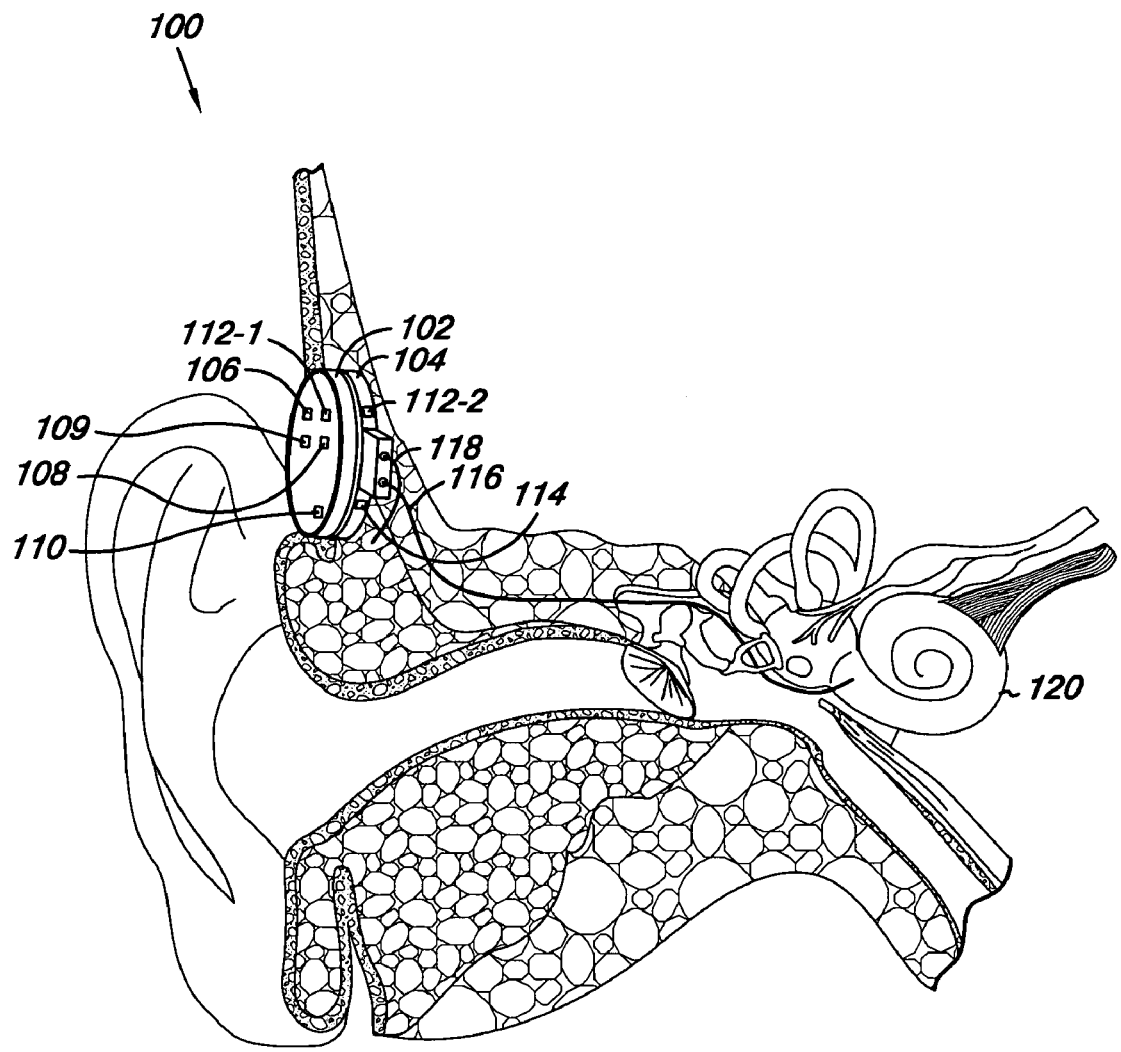
FIG. 1 illustrates a diagram of a cochlear implant system in accordance with one or more embodiments of the present disclosure.

The present disclosure includes methods, devices, and systems for cochlear implants. One method embodiment for cochlear implant signal processing includes processing a differential analog audio signal using amplitude modulation and pulse-width modulation. The method includes driving a transmission coil on an external unit of the cochlear implant with the pulse-width and amplitude modulated signal. The method also includes driving a reception coil on an internal unit of the cochlear implant with an output of the transmission coil.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10," in FIG. 1, and a similar element may be referenced as 210 in FIG. 2. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present invention, and should not be taken in a limiting sense.

FIG. 1 illustrates a diagram of a cochlear implant system in accordance with one or more embodiments of the present disclosure. A cochlear implant system 100 can include an external unit 102 and an internal unit 104. The external unit 102 can be worn by a patient external to the patient's body. The internal unit 104 can be surgically implanted under the patient's skin.

The external unit 102 can include a microphone 106, a processor 108, a battery 109, a transmitter 110, and a magnet 112-1. Although not illustrated in FIG. 1, the external unit 102 can also include a volume control that can be operated by a patient to control the level of volume received by the patient from the cochlear implant system 100. The external unit 102 can include a control that can be operated by the patient to select a hearing profile for use in, for example, a crowded room, a concert hall, etc.

The microphone 106 can receive an audio signal, e.g., sound such as speech, music, ambient noise, etc. The microphone 106 can be coupled to the processor 108 and to the battery 109.

The processor 108 can include a number of components such as an amplitude modulation circuit and a pulse-width modulation circuit as described herein. The processor 108 can receive signals, e.g., audio signals, from the microphone 106 and can function to process the signals for transmission to the internal unit 104. Accordingly, the processor 108 can be coupled to the transmitter 110 and to the battery 109. Processor 108 can be configured as an application specific integrated circuit (ASIC) and/or a number of discrete components coupled to a common substrate, among other configurations.

The external unit 102 can include one or more batteries 109. For example, the external unit 102 can include a number of 1.4 volt hearing aid-type batteries; however embodiments are not limited to a particular number or type of battery. The battery 109 can be coupled to one or more of the microphone 106, the processor 108, the transmitter 110, and the external magnet 112-1.

The transmitter 110 can be a transmission coil, e.g., an inductor. The transmitter 110 can be coupled to the processor 108 and receive a signal, e.g., a processed audio signal, therefrom. The transmitter 110 can transmit an electromagnetic (EM), e.g., a radio frequency (RF), signal to a receiver 114 in the internal unit 104. The transmitter 110 can be inductively coupled with the receiver 114 and provide power thereto.

The internal unit 104 can include a magnet 112-2, a receiver 114, a cochlear electrode 116, and a ground electrode 118. In one or more embodiments, the internal unit 104 does not include a battery, which can reduce time and expense associated with otherwise replacing components that are internal to the patient. In some embodiments, the internal unit 104 does not include signal processing circuitry, which can reduce the cost of the internal unit and allow it to function with different external units, e.g., external units that are developed after the internal unit 104 is implanted.

The external magnet 112-1 can interact with the internal magnet 112-2 to couple the external unit with the internal unit by magnetic force. That is the external unit 102 can be magnetically coupled with the internal unit 104 although there is no direct physical contact between the two components. The external magnet 112-1 and internal magnet 112-2 can align the external unit 102 and the internal unit 104 such that the transmitter 110 is aligned with the receiver 114. Such embodiments can be beneficial in helping to provide consistent signal quality of an EM signal between the transmitter 110 and the receiver 114.

The receiver 114 can be a reception coil configured to receive EM signals and/or power from the transmitter 110, e.g., transmission coil, by inductive coupling. The receiver 114 can output a signal to the cochlear electrode 116 for application to the cochlea 120.

The cochlear electrode 116 can be a single-channel short electrode that is coupled with the patient's cochlea 120. However, embodiments are not so limited as one or more embodiments can include multi-channel cochlear electrodes and/or long cochlear electrodes, among other types of electrodes. With respect to cochlear implants, a single channel short electrode is one that is only implanted into the cochlea 120 a few millimeters and can deliver an analog of sound. In contrast, a multichannel long electrode is one that may be implanted further into the cochlea 120 to deliver different frequencies, e.g., different digital channels, to different portions of the cochlea 120.

The cochlear electrode 116 can be coupled to the receiver 114 and receive a signal therefrom for application to the patient's cochlea 120, e.g., to apply sound to the patient. The ground electrode 118 can be an electrode that is implanted into the patient to provide an electrical ground for the internal unit 104. For example, the ground electrode 118 can be implanted in the patient's temporalis muscle as illustrated in FIG. 1. Embodiments are not so limited, e.g., the ground electrode 118 can be implanted elsewhere.

Figure 2A:
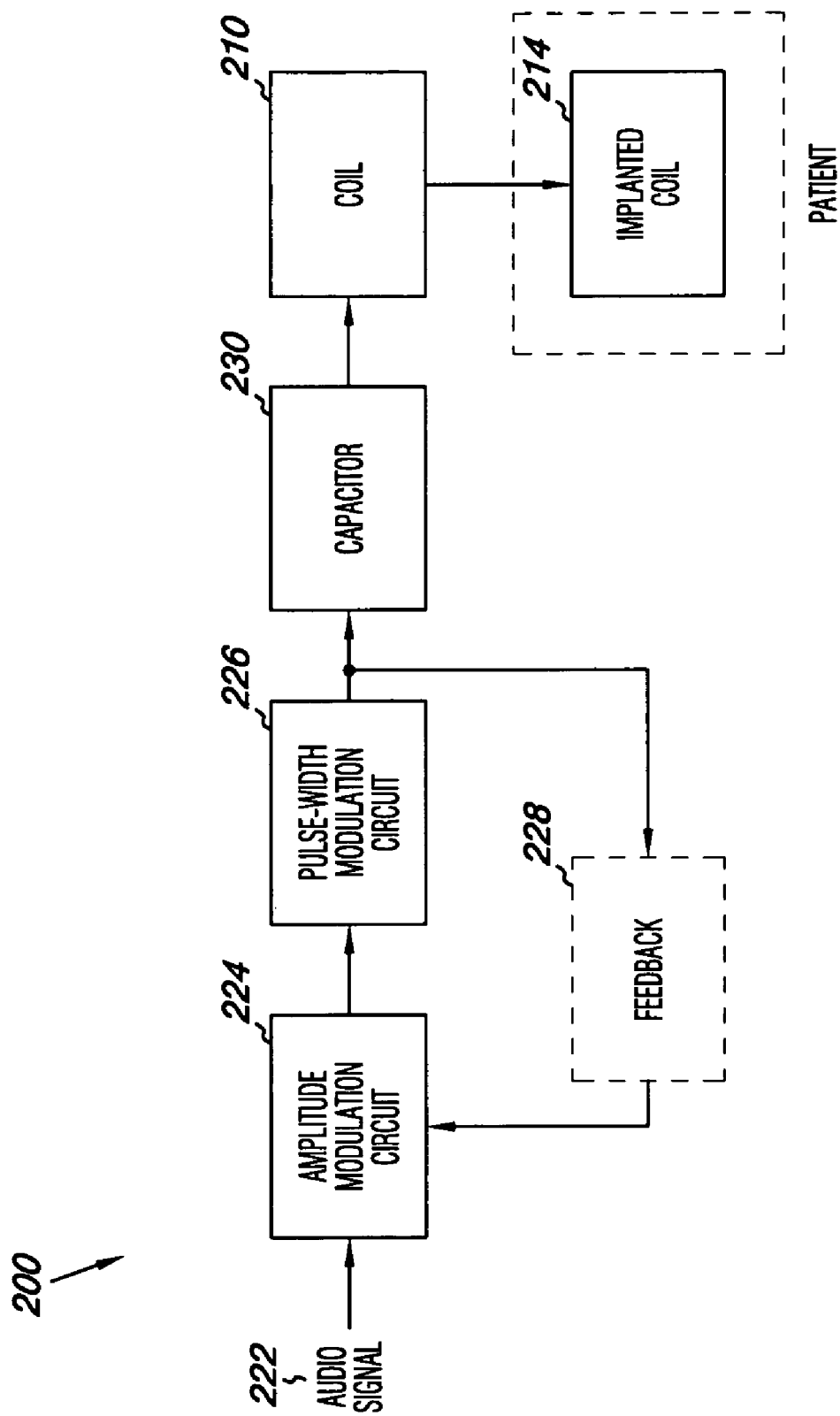
FIGS. 2A and 2B illustrate functional block diagrams of cochlear implant signal processing systems in accordance with one or more embodiments of the present disclosure.
Figure 2B:
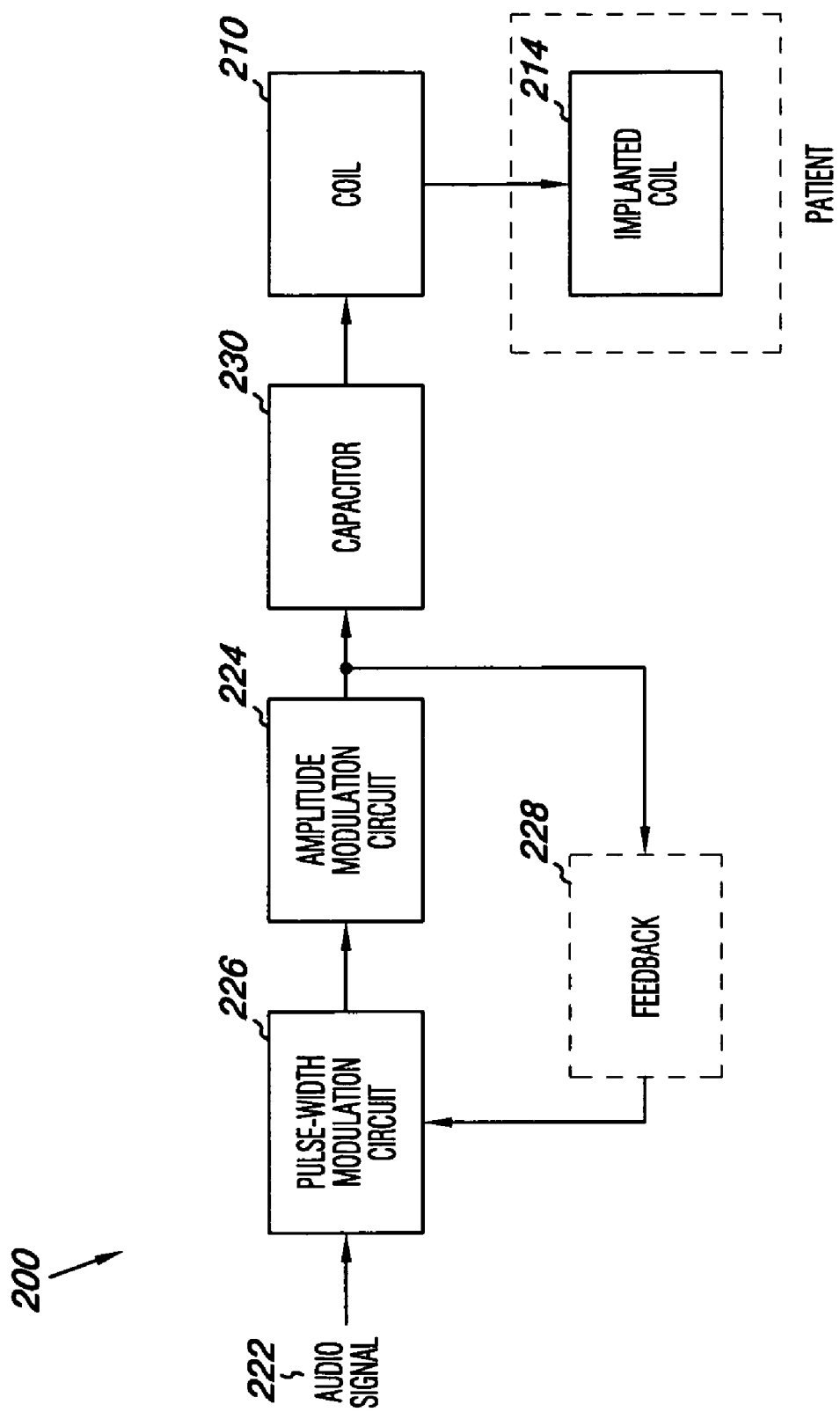

FIGS. 2A and 2B illustrate functional block diagrams of cochlear implant signal processing systems in accordance with one or more embodiments of the present disclosure. A cochlear implant signal processing system 200 can include a number of external components such as an audio signal 222, an amplitude modulation circuit 224, a pulse-width modulation circuit 226, a feedback loop 228, a capacitor 230, and an inductive coil 210.

The audio signal 222 can be an audio signal received from a microphone, e.g., microphone 106 in FIG. 1. The audio signal 222 can be a differential analog audio signal. In one or more embodiments, the audio signal 222 can be a processed audio signal, as will be understood by one of ordinary skill in the art. An illustration of an example analog audio signal is provided in FIG. 7.

With respect to the embodiment illustrated in FIG. 2A, the audio signal 222 can be input to the amplitude modulation circuit 224, which has an output to the pulse-width modulation circuit 226. The pulse-width modulation circuit 226 has an output to a capacitor 230 and inductive coil 210 combination.

The amplitude modulation circuit 224 can amplitude modulate a carrier signal with the audio signal 222. The amplitude modulation circuit can be coupled to a microphone, e.g., microphone 106 in FIG. 1, and receive the audio signal 222 therefrom. The amplitude modulation circuit 224 can be coupled to a number of batteries, e.g., battery 109 in FIG. 1, and receive power therefrom.

The pulse-width modulation circuit 226 can be coupled to the amplitude modulation circuit 224 and can pulse-width modulate a signal input from the amplitude modulation circuit 224 with a second signal, e.g., a sawtooth waveform signal. The pulse-width modulation circuit 226 can be coupled to a number of batteries, e.g., battery 109 in FIG. 1, and receive power therefrom.

The feedback loop 228 is illustrated in FIGS. 2A and 2B with a dashed line to indicate that it is an optional component of the cochlear implant signal processing system 200. In the embodiment illustrated in FIG. 2A, the feedback loop 228 can feedback an output of the pulse-width modulation circuit 226 as an input to the amplitude modulation circuit 224, e.g., to set an alternating current (AC) and/or direct current (DC) level of the audio signal 222 input to the amplitude modulation circuit 224 as is described in more detail herein. The output of the pulse-width modulation circuit 226 can be an amplitude modulated and pulse-width modulated audio signal, which can be fed back to the amplitude modulation circuit 224 to set an AC and/or DC current level for amplitude modulating the carrier signal. Using feedback loop 228 to set an AC and/or DC level of the audio signal 222 can be beneficial in helping to control the output of the pulse-width modulation circuit 226 such that it does not approach a sensitivity threshold of the cochlear implant signal processing system 200.

With respect to the embodiment illustrated in FIG. 2B, the audio signal 222 can be input to the pulse-width modulation circuit 226, which has an output to the amplitude modulation circuit 224. The amplitude modulation circuit 224 has an output to a capacitor 230 and inductive coil 210 combination.

The pulse-width modulation circuit 226 can pulse-width modulate the audio signal 222 with a second signal, e.g., a sawtooth waveform signal. The pulse-width modulation circuit 226 can be coupled to a number of batteries, e.g., battery 109 in FIG. 1, and receive power therefrom. An output of the pulse-width modulation circuit 226 can be input to the amplitude modulation circuit 224.

The amplitude modulation circuit 224 can amplitude modulate a carrier signal with the input from the pulse-width modulation circuit 226. The amplitude modulation circuit can be coupled to the capacitor 230 and inductive coil 210 combination. The amplitude modulation circuit 224 can be coupled to a number of batteries, e.g., battery 109 in FIG. 1, and receive power therefrom.

In the embodiment illustrated in FIG. 2B, the feedback loop 228 can feedback an output of the amplitude modulation circuit 224 as an input to the pulse-width modulation circuit 226, e.g., to set an alternating current (AC) and/or direct current (DC) level of the audio signal 222 input to the pulse-width modulation circuit 226 as is described in more detail herein. The output of the amplitude modulation circuit 224 can be a pulse-width modulated and amplitude modulated audio signal, which can be fed back to the pulse-width modulation circuit 226 to set an AC and/or DC current level for pulse-width modulating the audio signal 222. Using feedback loop 228 to set an AC and/or DC level of the audio signal 222 can be beneficial in helping to control the output of the amplitude modulation circuit 224 such that it does not approach a sensitivity threshold of the cochlear implant signal processing system 200.

The capacitor 230 can be used to tune an output frequency of the inductive coil 210 to a particular frequency, e.g., the capacitance of the capacitor 230 can be selected to provide a particular resonant frequency of the inductive coil 210. The inductive coil 210 can transmit a signal to an implanted coil 214. The implanted coil 214 can be a component of an internal unit of the cochlear implant signal processing system 200.

The inductive coil 210 can be a transmission coil, e.g., an inductor, coupled to an output of the pulse-width modulation circuit 226, e.g., via the capacitor 230. The inductive coil 210 can be configured to transmit an EM signal, e.g., to a receiver such as receiver 114 in FIG. 1. The receiver can be an implanted coil 214. The inductive coil 210 can be driven with the pulse-width and amplitude modulated signal that is output from the pulse-width modulation circuit 226 through the capacitor 230.

The combination of the capacitor 230 and the inductive coil 210 can be referred to as a tuned circuit, e.g., an LC (inductor, capacitor) circuit. In one or more embodiments, the tuned circuit can include a resistor, e.g., be coupled in series with a resistor such as resistor 450 in FIG. 4, to form an RLC (resistor, inductor, capacitor) circuit. The same is described in more detail in connection with FIG. 4.

The tuned circuit can be coupled to the pulse-width modulation circuit 226. In one or more embodiments, the tuned circuit can be configured to transmit a signal corresponding to the pulse-width and amplitude modulated signal.

The implanted coil 214 is illustrated in FIGS. 2A and 2B as being within a dashed line labeled "Patient" to indicate that the implanted coil 214 is part of an internal, e.g., implanted, unit of the cochlear implant signal processing system 200. In one or more embodiments, the implanted coil 214 can be a reception coil configured to receive the EM signal transmitted by the transmission coil. The implanted coil 214 can be driven with the output of the external transmission coil 210. The implanted coil 214, e.g., the reception coil, can drive an electrode, e.g., cochlear electrode 116 in FIG. 1, according to the output of the inductive coil 210, e.g., the transmission coil. Driving the electrode can include outputting an analog AM signal from the implanted coil 214 to the electrode.

Figure 3:
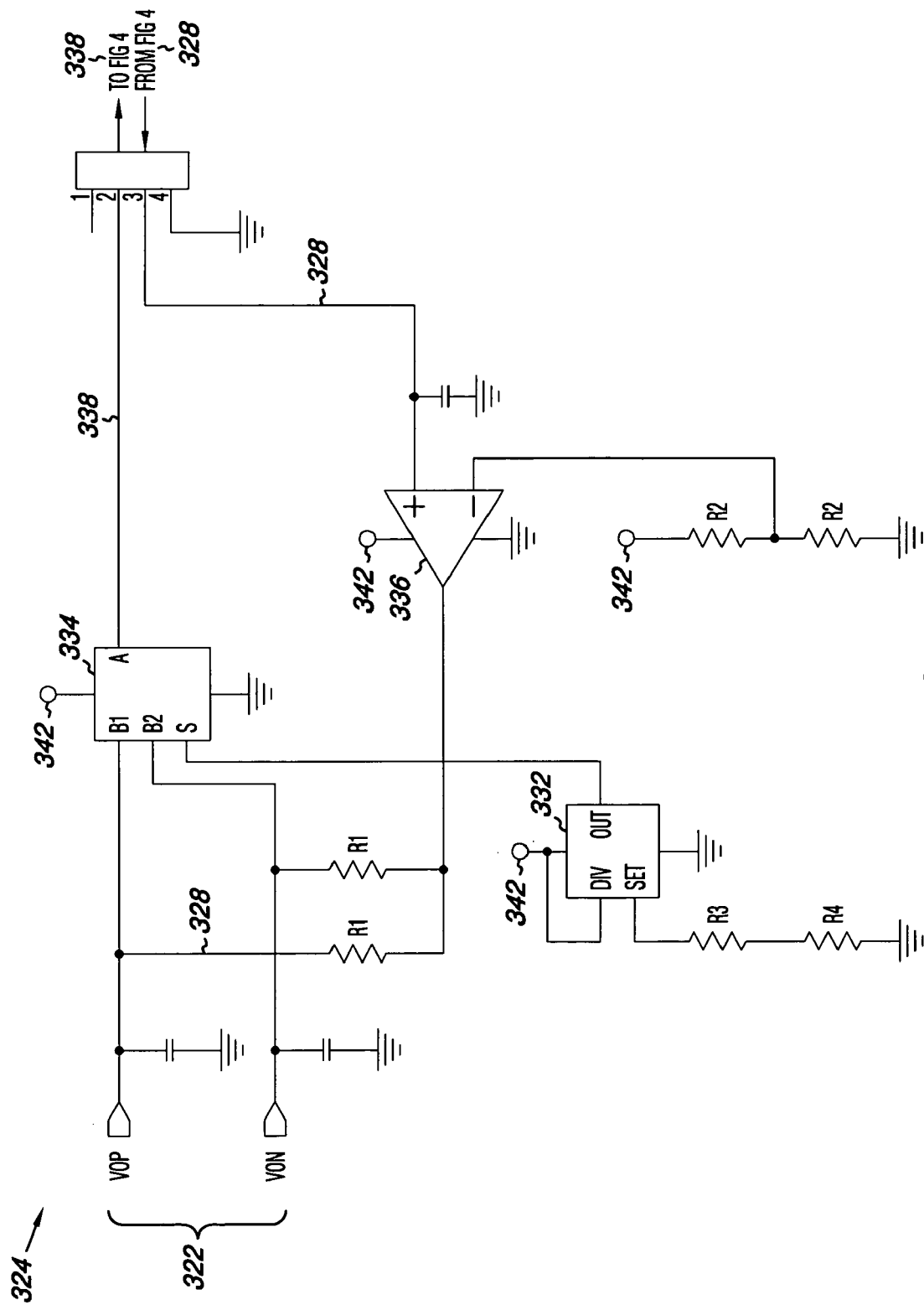
FIG. 3 illustrates a diagram of an amplitude modulation circuit in accordance with one or more embodiments of the present disclosure.

FIG. 3 illustrates a diagram of an amplitude modulation circuit in accordance with one or more embodiments of the present disclosure. As will be appreciated, the amplitude modulation circuit 324 illustrated in FIG. 3 is one example configuration of an amplitude modulation circuit that includes double-sideband suppressed-carrier amplitude modulation. The case of suppressed-carrier modulation is one subset of reduced-carrier modulation wherein the spectral content contains operatively no carrier energy. One or more embodiments of the present disclosure can include an alternate amplitude modulation circuit, for example, amplitude modulation circuits that provide single-sideband reduced-carrier, single-sideband full-carrier, single-sideband suppressed-carrier, independent-sideband emission, and/or vestigal-sideband, among others.

An advantage of a reduced-carrier and/or a suppressed-carrier modulation approach over some previous approaches is that analog information can be preserved while reducing overall power consumption. A further advantage of such embodiments is that when audio is not present, there is less or no signal delivered to the cochlea. A reduced-carrier amplitude modulated signal can have a carrier level reduced below a carrier level associated with an amplitude modulator for the differential analog audio signal, according to one or more embodiments of the present disclosure.

One or more embodiments of the present disclosure can include a fully implantable cochlear implant that can operate with the audio signal 222 and amplitude modulation circuit 224 of FIG. 2A. In such embodiments, the amplitude modulated audio signal output from the amplitude modulation circuit 224 can be analogous to the signal shown in FIG. 8 and can be directly applied through one or more electrodes to the cochlea. Such an embodiment for a fully implantable cochlear implant can preserve the advantages described herein with respect to a reduced-carrier or suppressed-carrier modulation approach. As a fully implantable cochlear implant does not transmit the modulated audio information across the patient's skin, the pulse-width modulation circuit 226, transmission coil 210, or receiver coil may not be included with such embodiments.

The amplitude modulation circuit 324 can be analogous to amplitude modulation circuit 224 illustrated in FIG. 2A. For example, the amplitude modulation circuit 324 can include a differential audio signal 322 input, e.g., audio signal 222 in FIG. 2A, and an output 338 to a pulse width modulation circuit, e.g., pulse width modulation circuit 226 illustrated in FIG. 2A. One or more embodiments can include a differential analog audio signal 322 input, e.g., VOP and VON as illustrated in FIG. 3. A differential signal is a signal that is transmitted as a set of two complimentary signals, e.g., using two separate wires. For example, VOP may be a complimentary, e.g., opposite, signal with respect to VON. As described herein, the audio signal 322 can be received directly from a microphone, e.g., microphone 106 in FIG. 1. However embodiments are not so limited, as the audio signal 322 can be received from signal processing circuitry coupled to a microphone.

The audio signal 322 can be input to a switch 334, e.g., an amplitude modulator. The audio signal 322 can be input as a differential signal VOP (B1) and VON (B2). Using differential signaling, as opposed to single-ended signaling, can provide a number of advantages. For example, with differential signaling, a signal may not be compared to a ground reference, so any variations in the ground potential may not affect the differential signal. Another advantage of differential signaling is that it can provide improved noise immunity over single-ended signaling because the useful voltage range for a given supply voltage, e.g., Vs, is +Vs to −Vs, as opposed to single-ended signaling, where the useful voltage range would be +Vs to ground, e.g., 0 V.

The switch 334 can include an input (S) from oscillator 332, e.g., a programmable oscillator. In one or more embodiments, the switch 334 can be a single-pole double-throw analog switch. The switch 334 can amplitude modulate the signal output from the oscillator 332, e.g., the carrier signal, with the audio signal 322 to output (A) an amplitude modulated signal 338. Accordingly, the oscillation frequency from oscillator 332 can determine the frequency of amplitude modulation.

In one or more embodiments, the oscillator 332 can be a resistor set oscillator, e.g., one or more resistors such as R3 and R4 can be used to set (SET) the output frequency (OUT) of the oscillator 332 for a given power supply 342 (DIV). Example values for R3 and R4 are 220 kΩ and 124 kΩ respectively however embodiments are not so limited. The oscillator 332 can be configured to generate a carrier signal for the amplitude modulation circuit 324.

Figure 4:
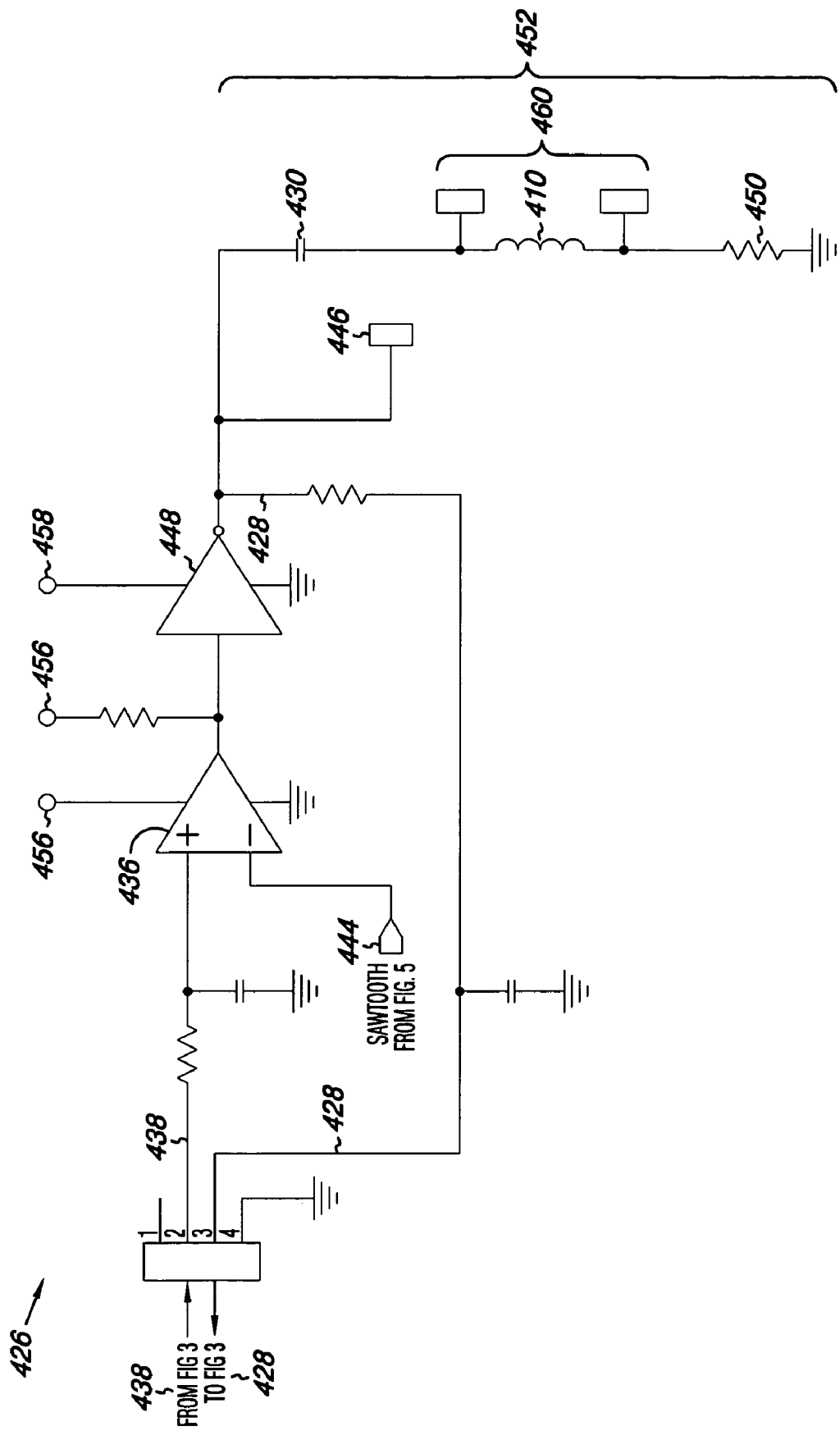
FIG. 4 illustrates a diagram of a pulse-width modulation circuit and a tuned circuit in accordance with one or more embodiments of the present disclosure.

The amplitude modulated audio signal 338 can be fed to a pulse-width modulation circuit, e.g., pulse-width modulation circuit 426 illustrated in FIG. 4. An illustration of a carrier signal amplitude modulated with the example audio signal provided in FIG. 7, e.g., an amplitude modulated audio signal, is provided in FIG. 8.

The amplitude modulation circuit 324 illustrated in FIG. 3 includes a feedback loop 328 with an input from the pulse-width modulation circuit 426 illustrated and described in more detail with FIG. 4. The feedback loop 328 is fed into a comparator 336 and output to mix with the audio signal 322 input to the switch 334. For example, the comparator 336 can be a 1.8 volt comparator with a rail to rail input.

As illustrated in FIG. 3, one input to the comparator 336 can be the feedback signal 328, while the other input can be an output of a voltage divided power supply 342. As illustrated, the voltage divider includes two resistors, R2, of the same value, thus the power supply 342 is divided in half in this example embodiment, however embodiments are not so limited. An example value for R2 is 270 kΩ, however embodiments are not so limited. Such embodiments may be useful where a target voltage of the feedback signal 328 from an inverter, e.g., inverter 448 described in more detail in association with FIG. 4, is approximately equal to half of the supply voltage. For example, the supply voltage may be 2.8 volts and the voltage of the feedback signal 328 may be approximately 1.0 volts.

In one or more embodiments, the feedback loop 328 and comparator 336 can be used to help adjust an AC and/or DC voltage of the audio signal 322 before the switch 334. Feedback loop 328 can help match the AC and/or DC voltage of the audio signal 322 and that of the sawtooth input, e.g., sawtooth input 444 in FIG. 4, to levels suitable for switch 334 so that the output of inverter 448 in FIG. 4 is closer to the target.

The feedback loop 328 can mix with each complimentary signal, e.g., VOP and VON, of the differential audio signal 322. As illustrated in FIG. 3, the output of the comparator 336 on feedback loop 328 can mix with each complimentary signal, e.g., VOP and VON, through a resistor having a common value (R1). An example value for R1 is 470 kΩ, however embodiments are not so limited. Such embodiments can be beneficial in allowing the feedback loop 328 to have the same relative effect on each complimentary signal to the switch 334, however embodiments are not so limited. Mixing the feedback loop 328 with the audio signal 322 can allow a DC and/or AC level of the audio signal 322 to be set. Such embodiments can be beneficial in controlling the range of the audio signal 322 so that it falls within an operating range of the switch 334.

The switch 334, the comparator 336, the oscillator 332, and the voltage divider can have inputs from a power supply 342. The power supply 342 can be derived from one or more batteries, e.g., battery 109 in FIG. 1. Although a same power supply 342 is illustrated for each of these components, embodiments are not so limited. An appropriate power supply can be provided for each component from the one or more batteries as will be understood by one of ordinary skill in the art.

The amplitude modulation circuit 324 illustrated in FIG. 3 includes a number of grounded capacitors coupled to the circuit. One of ordinary skill in the art will appreciate that such components can be used to smooth a signal at various points in the circuit and do not limit the scope of this disclosure.

FIG. 4 illustrates a diagram of a pulse-width modulation circuit and a tuned circuit in accordance with one or more embodiments of the present disclosure. As will be appreciated, the pulse-width modulation circuit 426 illustrated in FIG. 4 is one example configuration of a pulse-width modulation circuit that uses a sawtooth wave and trailing edge modulation. One or more embodiments of the present disclosure can include an alternate pulse-width modulation circuit, for example, centered modulation, e.g., using a triangle wave, and leading edge modulation, among other embodiments.

The pulse-width modulation circuit 426 includes, as an input, an output 438 from the amplitude modulation circuit 324 in FIG. 3. The pulse-width modulation circuit 426 also includes a portion of the feedback loop 428, which is output to the amplitude modulation circuit 324 in FIG. 3. That is, feedback loop 328 in FIG. 3 is a portion of the total feedback loop, another portion of which is illustrated as feedback loop 428 in FIG. 4. Likewise, the output 338 of the amplitude modulation circuit 324 in FIG. 3 is the same as the input from the amplitude modulation circuit, illustrated as 438 in FIG. 4.

The output 438 from the amplitude modulation circuit, e.g., the carrier signal amplitude modulated with the audio signal, can be input to a comparator 436 along with an output signal 444, e.g., an output from a sawtooth wave generator. The comparator can have an input from a power supply 456. The comparator 436 having said inputs can be configured to modulate the amplitude modulated signal 438 with the sawtooth signal 444. For example, the comparator 436 can be configured to use trailing edge modulation such that when the value of the amplitude modulated signal 438 is greater than the sawtooth signal 444, the output of the comparator 436 is high and when the value of the amplitude modulated signal 438 is less than the sawtooth signal 444, the output of the comparator 436 is low. Accordingly, such pulse-width modulation can be said to create a digital signal. However, as described in more detail herein, aspects of the transmission of the output of the comparator 436 and reception thereof remain analog in nature.

Figure 9:
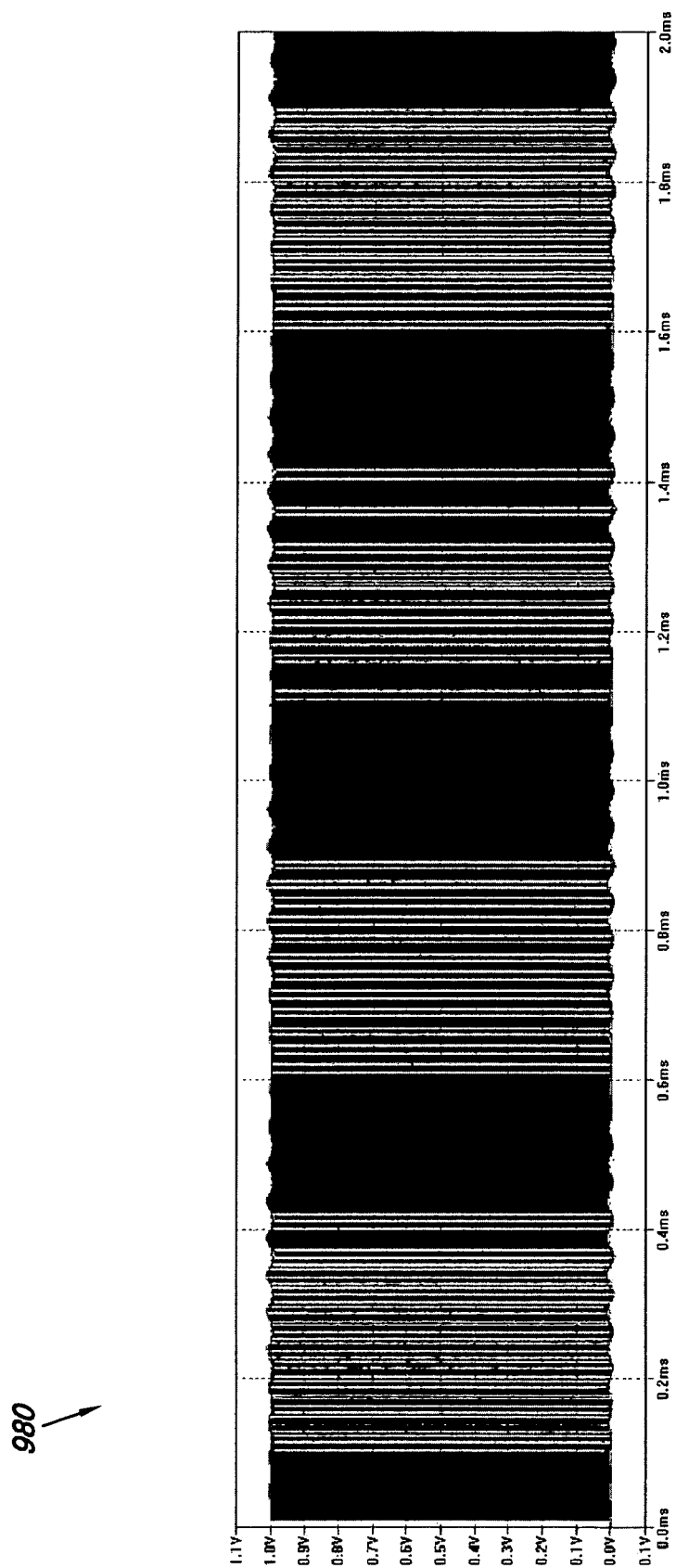
FIG. 9 illustrates a diagram of the amplitude modulated signal of FIG. 8 after pulse-width modulation in accordance with one or more embodiments of the present disclosure.
Figure 10A:
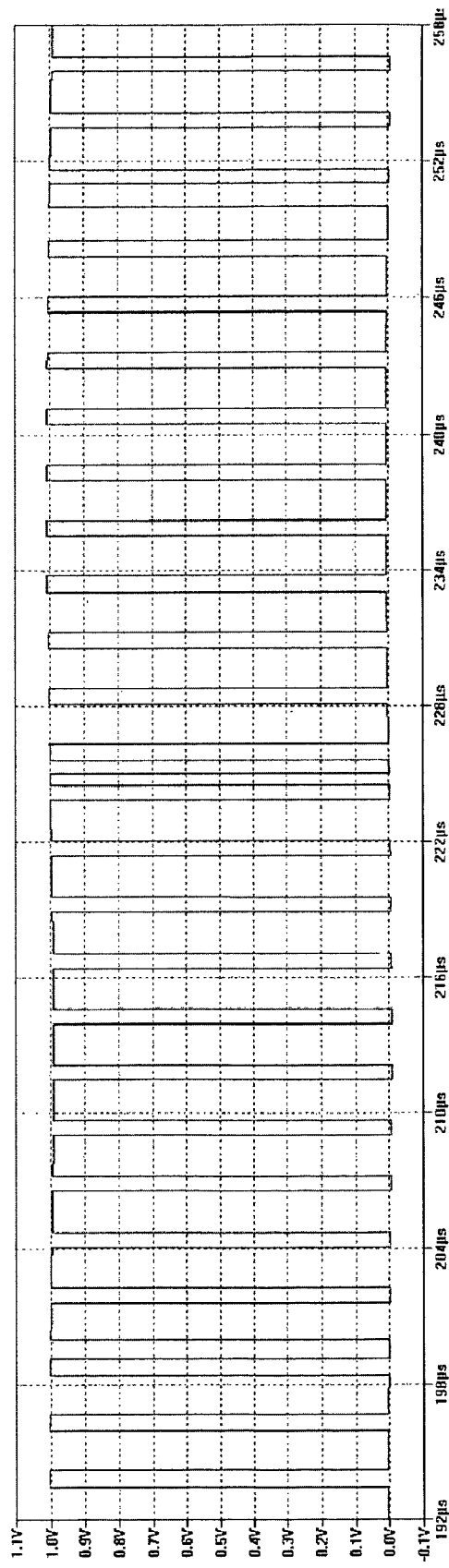
FIG. 10A illustrates a diagram of a portion of the signal illustrated in FIG. 9 in accordance with one or more embodiments of the present disclosure.

The output of the comparator 436 can be inverted by an inverter 448 and passed along the feedback loop 428, e.g., back to the amplitude modulation circuit 324 in FIG. 3. The operation of the comparator 436 and inverter 448 can serve to pulse-width modulate the signal 438. The inverter 448 can have an input from a power supply 458, which can be the same or different from the power supply 456. The inverted output can be observed at test pad 446, e.g., as illustrated in FIGS. 9 and 10A.

After the inverter 448, the signal can be applied to a tuned circuit 452, e.g., an LC or RLC circuit. The tuned circuit 452 can include a capacitor 430, an inductor, e.g., inductive coil, 410, and a resistor 450 coupled in series. In one or more embodiments, the tuned circuit 452 does not include a resistor and operates as an LC circuit rather than as an RLC circuit.

The tuned circuit 452 can operate to transmit a signal from an external unit of a cochlear implant system to an internal unit. In one or more embodiments, the tuned circuit 452 can be tuned by one or more of the capacitor 430 and the resistor 450 such that the inductive coil 410 has a particular natural resonant frequency approximately equal to the amplitude modulation frequency, e.g., the frequency of the carrier signal generated by the oscillator 332 in FIG. 3. Illustrations of an example output of the transmission coil 410, e.g., the signal between test points 460, are provided in FIGS. 11 and 12.

For embodiments where the tuned circuit 452 is an LC circuit, the capacitance of the capacitor 430 can be selected, e.g., in the case of a static capacitor, or adjusted, e.g., in the case of a variable capacitor, to tune the resonant frequency of the inductive coil 410. Likewise, for embodiments where the tuned circuit 452 is an RLC circuit, the capacitance of the capacitor 430 can be provided as described for the LC circuit while the resistance of the resistor 450 can be selected, e.g., in the case of a static resistor, or adjusted, e.g., in the case of a variable resistor such as a potentiometer, to tune the quality factor (Q factor), which can determine how energy is dissipated. For example, if less current is desired in the implanted coil, an increased resistance of the resistor 450 can be selected to decrease the Q factor.

Such embodiments can be beneficial in providing for transmission of a signal from an external unit of a cochlear implant to an internal unit of a cochlear implant while using less power than would be used if the signal were amplitude modulated and transmitted without pulse-width modulation. That is, the combination of the amplitude modulation circuit 324 and the pulse-width modulation circuit 426 can provide an ability for the inductive coil 410 to transmit a signal to an implanted coil, e.g., coil 214 in FIGS. 2A and 2B, using a particular battery voltage, e.g., two 1.4 volt hearing aid batteries providing a total of 2.8 volts, rather than including one or more amplifiers to increase the power of an amplitude modulated signal, which may be included with some previous approaches.

Figure 8:
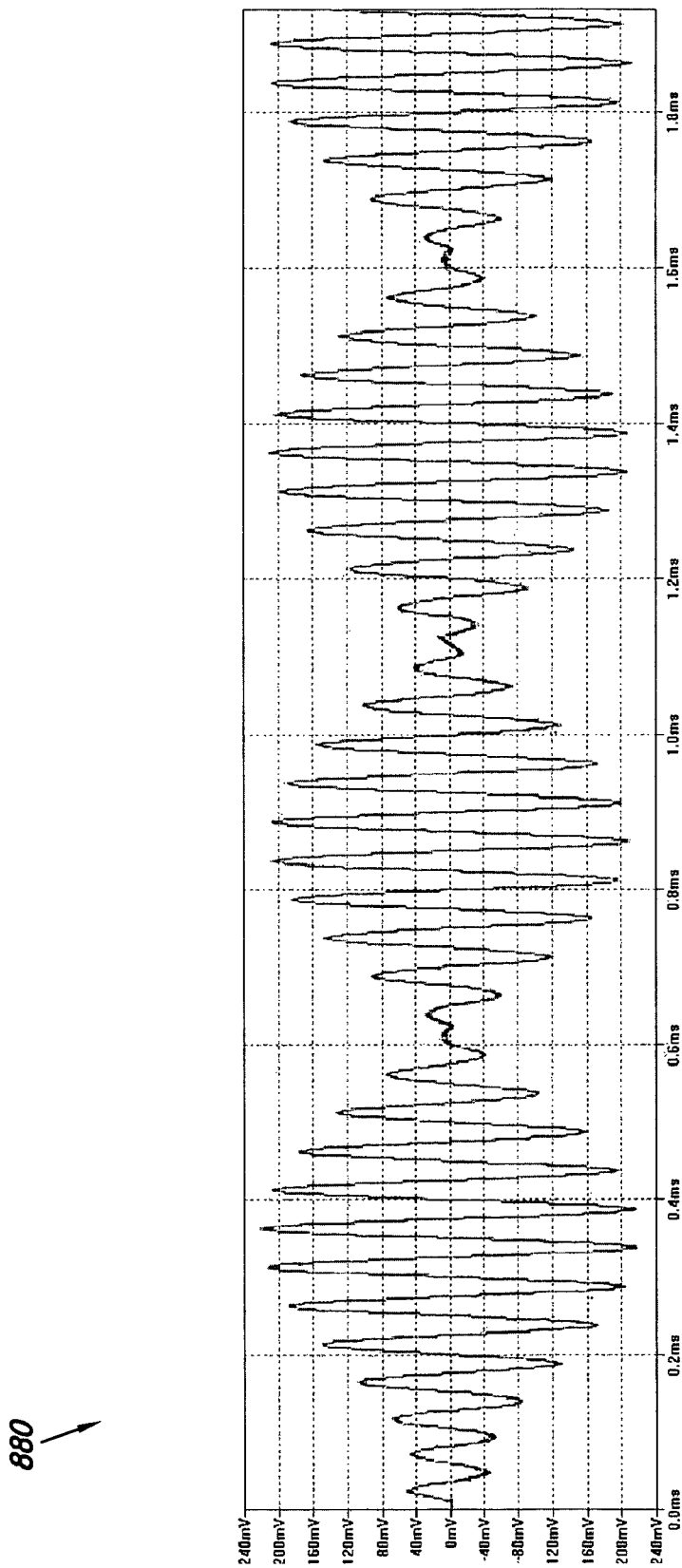
FIG. 8 illustrates a diagram of a carrier signal amplitude modulated with the audio signal of FIG. 7 in accordance with one or more embodiments of the present disclosure.
Figure 11:
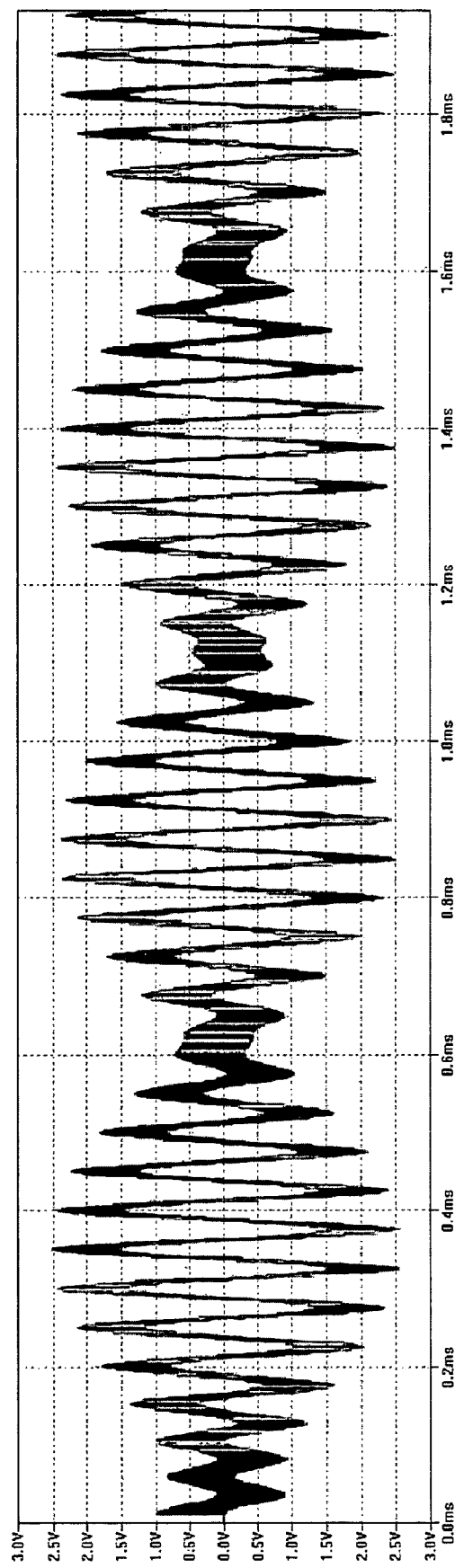
FIG. 11 illustrates a diagram of an amplitude and pulse-width modulated signal as output from a transmission coil in accordance with one or more embodiments of the present disclosure.

Furthermore, tuning the inductive coil 410 to resonate at a frequency approximately equal to the amplitude modulation frequency can allow for transmission of the pulse-width modulated signal, e.g., a digital signal, to appear as an analog amplitude modulated signal as can be seen in a comparison of FIG. 8 (an example amplitude modulated signal) and FIG. 11 (an example output of inductive coil 410). That is, the implanted coil, e.g., implanted coil 214 in FIGS. 2A and 2B, can receive the transmitted audio signal as an amplitude modulated signal appropriate for driving a cochlear electrode, e.g., a single-channel short electrode, of a cochlear implant system.

The pulse-width modulation circuit 426 illustrated in FIG. 4 includes a number of grounded capacitors coupled to the circuit. One of ordinary skill in the art will appreciate that such components can be used to smooth a signal at various points in the circuit and do not limit the scope of this disclosure.

Figure 5:
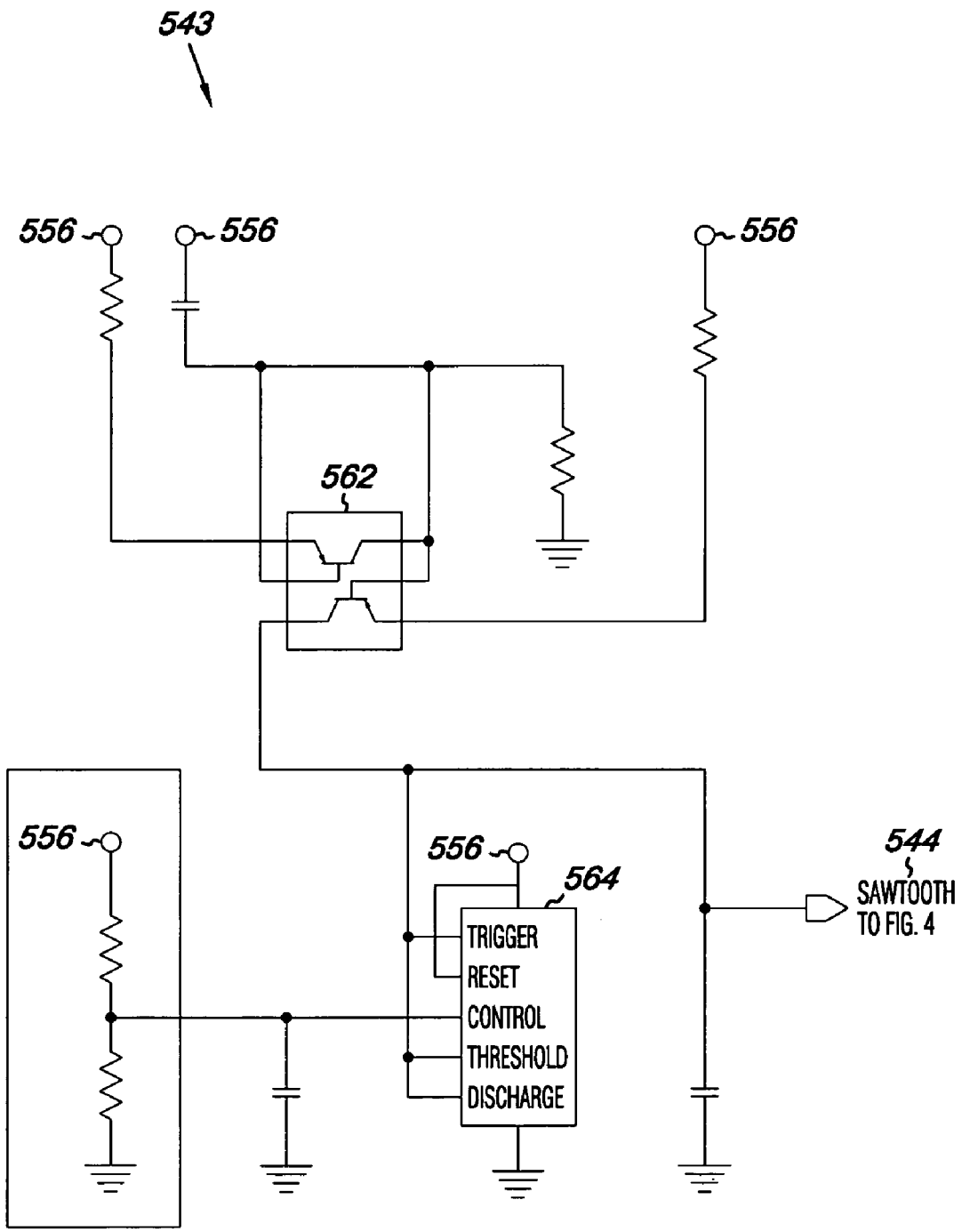
FIG. 5 illustrates a diagram of a sawtooth wave generator in accordance with one or more embodiments of the present disclosure.

FIG. 5 illustrates a diagram of a sawtooth wave generator in accordance with one or more embodiments of the present disclosure. A sawtooth wave generator 543 can include a switch 562 and a timer 564 that can be configured to generate a sawtooth wave signal 544 that can be output to a pulse-width modulation circuit, e.g., pulse-width modulation circuit 426 in FIG. 4. Embodiments are not limited to the specific configuration of the sawtooth wave generator 543 illustrated in FIG. 5 as other implementations can be provided by one of ordinary skill in the art.

The switch 562 can be a high speed switch such as a PNP bipolar junction transistor array, as will be appreciated by one of ordinary skill in the art. The switch 562, along with the resistors, can create a current source, which can help in setting the sawtooth frequency. The switch 562 can receive power from a number of power supplies 556 and be coupled to a timer 564. Timer 564 can be a low power complimentary metal oxide semiconductor (CMOS) timer.

The voltage divider coupled to the control input of the timer 564, illustrated in a box on the left side of FIG. 5, can be an optional component for controlling a voltage input to the timer 564, e.g., from a power supply 556.

Figure 6:
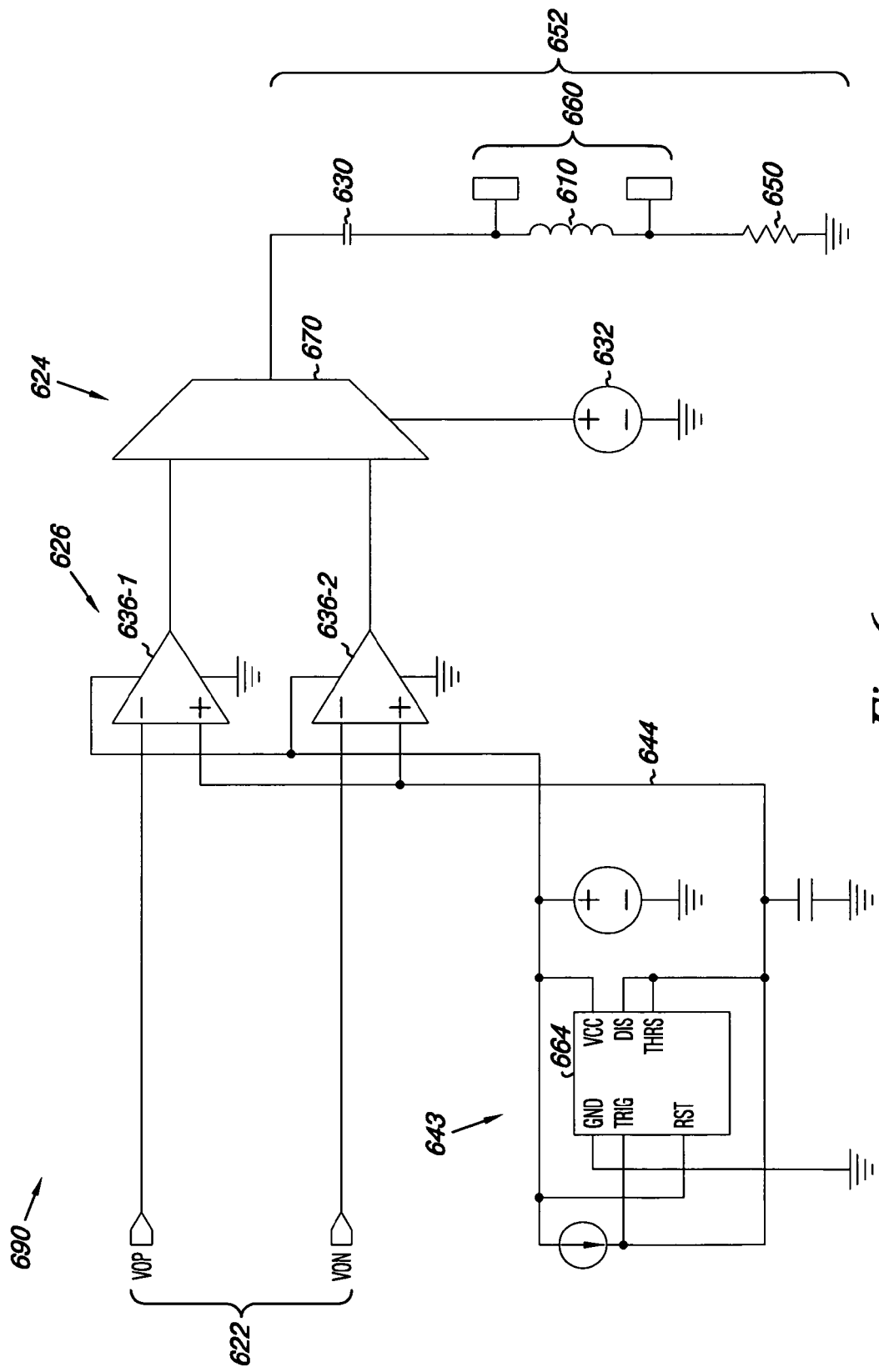
FIG. 6 illustrates a diagram of a cochlear implant signal processing circuit in accordance with one or more embodiments of the present disclosure.
Figure 7:
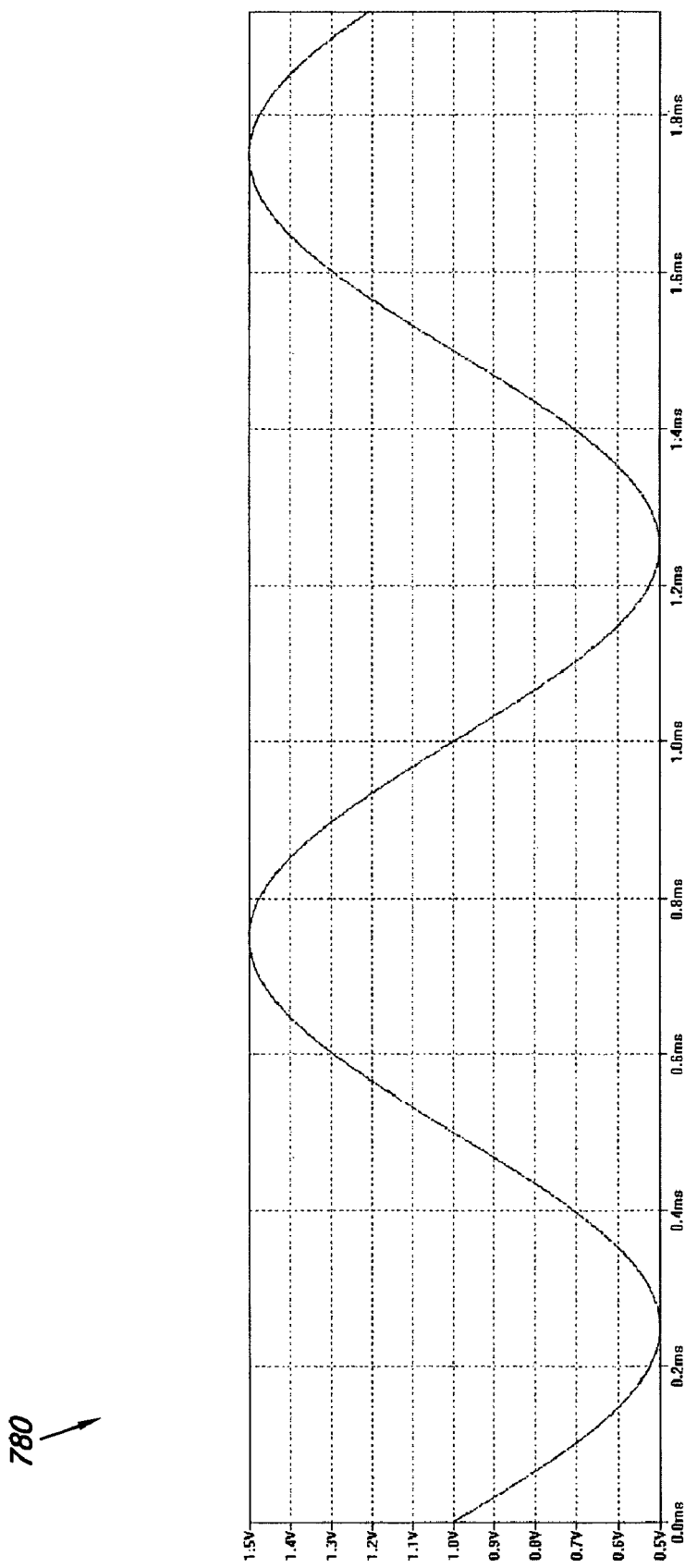
FIG. 7 illustrates a diagram of an analog audio signal in accordance with one or more embodiments of the present disclosure.

FIG. 6 illustrates a diagram of a cochlear implant signal processing circuit in accordance with one or more embodiments of the present disclosure. A cochlear implant signal processing circuit 690 can include a number of components such as a sawtooth wave generator 643, a pulse-width modulation circuit 626, an amplitude modulation circuit 624, and a tuned circuit 652. Some embodiments can include a differential analog audio signal 622 (VOP and VON) input to the pulse-width modulation circuit 626. An example of a complimentary signal of the differential analog audio signal 622 is illustrated in FIG. 7.

The pulse-width modulation circuit 626 can include a number of comparators, e.g., comparators 636-1 and 636-2. Each comparator 636-1 and 636-2 can have an input from a complimentary signal, e.g., VOP or VON, of the differential analog audio signal 622. Each comparator 636-1 and 636-2 can have an input, e.g., sawtooth input 644, from the sawtooth wave generator 643. In one or more embodiments, as illustrated in FIG. 6, the comparators 636-1 and 636-2 can receive power from a power source associated with the sawtooth wave generator 643, however embodiments are not so limited.

The comparators 636-1 and 636-2 can have analogous functionality to the comparator 436 in pulse-width modulation circuit 426 in FIG. 4. For example, the comparators 636-1 and 636-2 can be configured to modulate a complimentary signal of the differential analog audio signal 622 with the sawtooth signal 644. For example, the comparators 636-1 and 636-2 can be configured to use trailing edge modulation such that when the value of the audio signal 622 is greater than the sawtooth signal 644, the output of a comparator, e.g., comparator 636-1, is high and when the value of the audio signal 622 is less than the sawtooth signal 644, the output of the comparator, e.g., 636-1 is low. An illustrative representation of the output of comparator 636-1 for the audio signal input illustrated in FIG. 7 is provided in FIG. 10B. Embodiments are not limited to this particular implementation of pulse-width modulation.

The sawtooth wave generator 643 can have analogous functionality to the sawtooth wave generator 543 illustrated in FIG. 5. The sawtooth wave generator 643 can include a timer 664, which can be configured to generate a sawtooth wave signal 644 that can be input the to the comparators 636-1 and 636-2 in the pulse-width modulation circuit 626. The timer 664 can be a low power complimentary metal oxide semiconductor (CMOS) timer.

The comparators 636-1 and 636-2 can each output a pulse-width modulated signal to the amplitude modulation circuit 624. In one or more embodiments, the amplitude modulation circuit can include a digital multiplexer 670, e.g., a 2-to-1 multiplexer. Multiplexer 670 can time-division multiplex the pulse-width modulated signals, e.g., digital signals, from comparators 636-1 and 636-2 according to a select signal from a pulsed power supply 632, e.g., an oscillator, running at a carrier frequency for amplitude modulation.

The output of multiplexer 670 can include one analog signal that includes two channels, e.g., one channel corresponding to each input from comparators 636-1 and 636-2. The output of multiplexer 670 can drive to the tuned circuit 652. In one or more embodiments, the cochlear implant signal processing circuit 690 can include a feedback loop analogous to the feedback loop 228/328/428 illustrated in FIGS. 2, 3 and 4.

The tuned circuit 652, e.g., an LC or RLC circuit, can be analogous to the tuned circuit 452 in FIG. 4. The tuned circuit 652 can include a capacitor 630, an inductor, e.g., inductive coil, 610, and a resistor 650 coupled in series. In one or more embodiments, the tuned circuit 652 does not include a resistor and operates as an LC circuit rather than as an RLC circuit.

Figure 12:
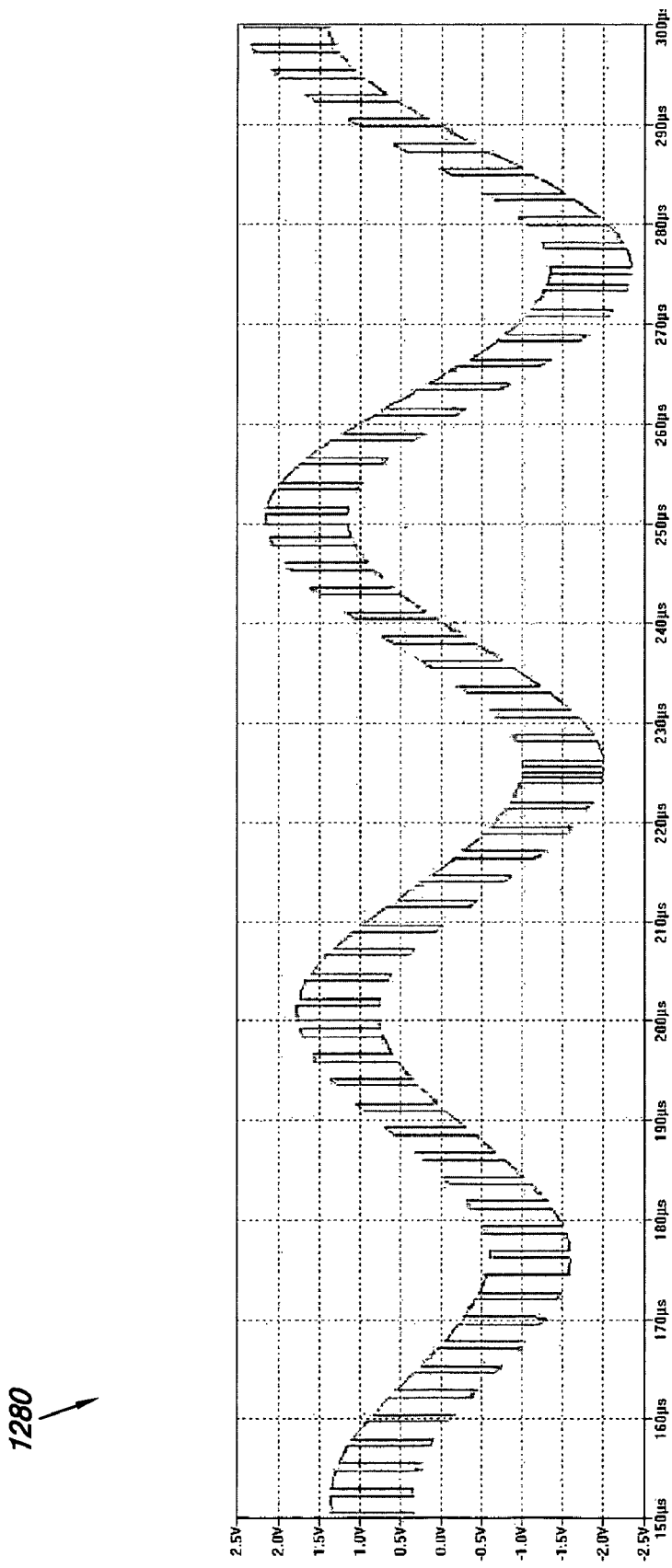
FIG. 12 illustrates a diagram of a portion of the signal illustrated in FIG. 11 in accordance with one or more embodiments of the present disclosure.

According to one or more embodiments of the present disclosure, the output of the inductive coil 610 can be analogous to the output of inductive coil 410 in FIG. 4 for an analogous audio input, e.g., the audio signal illustrated in FIG. 7. That is, the output of inductive coil 610, e.g., as measured at test pads 660, for such an audio input is illustrated in FIGS. 11 and 12.

FIG. 7 illustrates a diagram of an analog audio signal in accordance with one or more embodiments of the present disclosure. As will be appreciated, the diagram 780 of the analog audio signal, e.g., audio signal 222 in FIGS. 2A and 2B, is a 1000 hertz audio tone. The diagram 780 of the analog audio signal is an example of complimentary signal VOP of audio signal 322 in FIG. 3 and VOP of audio signal 622 in FIG. 6.

The audio signal is provided as an example to illustrate the function of a number of components of one or more embodiments of the present disclosure. For example, illustrations of signals associated with the operation of a number of components of one or more embodiments of the present disclosure with respect to the audio signal are provided in FIGS. 8-12.

FIG. 8 illustrates a diagram of a carrier signal amplitude modulated with the audio signal of FIG. 7 in accordance with one or more embodiments of the present disclosure. The diagram 880 shows the result of amplitude modulating a 20 kilohertz carrier signal, e.g., a carrier signal generated by oscillator 332 in FIG. 3, with the 1000 hertz audio signal illustrated in FIG. 7.

The diagram 880 can represent an example output, e.g., output 338 in FIG. 3, of an amplitude modulation circuit e.g., amplitude modulation circuit 224 in FIG. 2A. The signal illustrated in diagram 880 can be input to a pulse-width modulation circuit, e.g., pulse-width modulation circuit 226 in FIG. 2A.

FIG. 9 illustrates a diagram of the amplitude modulated signal of FIG. 8 after pulse-width modulation in accordance with one or more embodiments of the present disclosure. The diagram 980 shows the result of pulse-width modulating the amplitude modulated signal illustrated in FIG. 8 with a sawtooth wave, e.g., a sawtooth wave generated by the sawtooth wave generator 543 illustrated in FIG. 5.

The diagram 980 illustrates an example signal that could be observed from test pad 446 in FIG. 4. The pulse-width modulated signal illustrated in diagram 980 can be input to a tuned circuit, e.g., tuned circuit 452 in FIG. 4. The pulse-width modulated signal can optionally be fed back as an input to the amplitude modulation circuit, e.g., in a feedback loop 228 illustrated in FIG. 2A.

The diagram 980 illustrates a signal with the same scale as diagram 780 in FIG. 7 and diagram 880 in FIG. 8. As the details of the signal in diagram 980 may be difficult to observe, a "zoomed in" image of the signal is provided in FIG. 10A in a narrower scale.

FIG. 10A illustrates a diagram of a portion of the signal illustrated in FIG. 9 in accordance with one or more embodiments of the present disclosure. The diagram 1080-A provides additional detail on the signal image to illustrate the digital nature of the signal after pulse-with modulation.

Pulse-width modulation of the amplitude-modulated signal can provide a low power output to the tuned circuit. Note, for example, that the value of the pulse-width modulated signal in diagram 1080-A ranges from approximately 0-1 volts. This can be compared with the voltage across a transmission coil, e.g., inductive coil 410 in FIG. 4, as will be discussed below in connection with FIGS. 11 and 12.

Figure 10B:
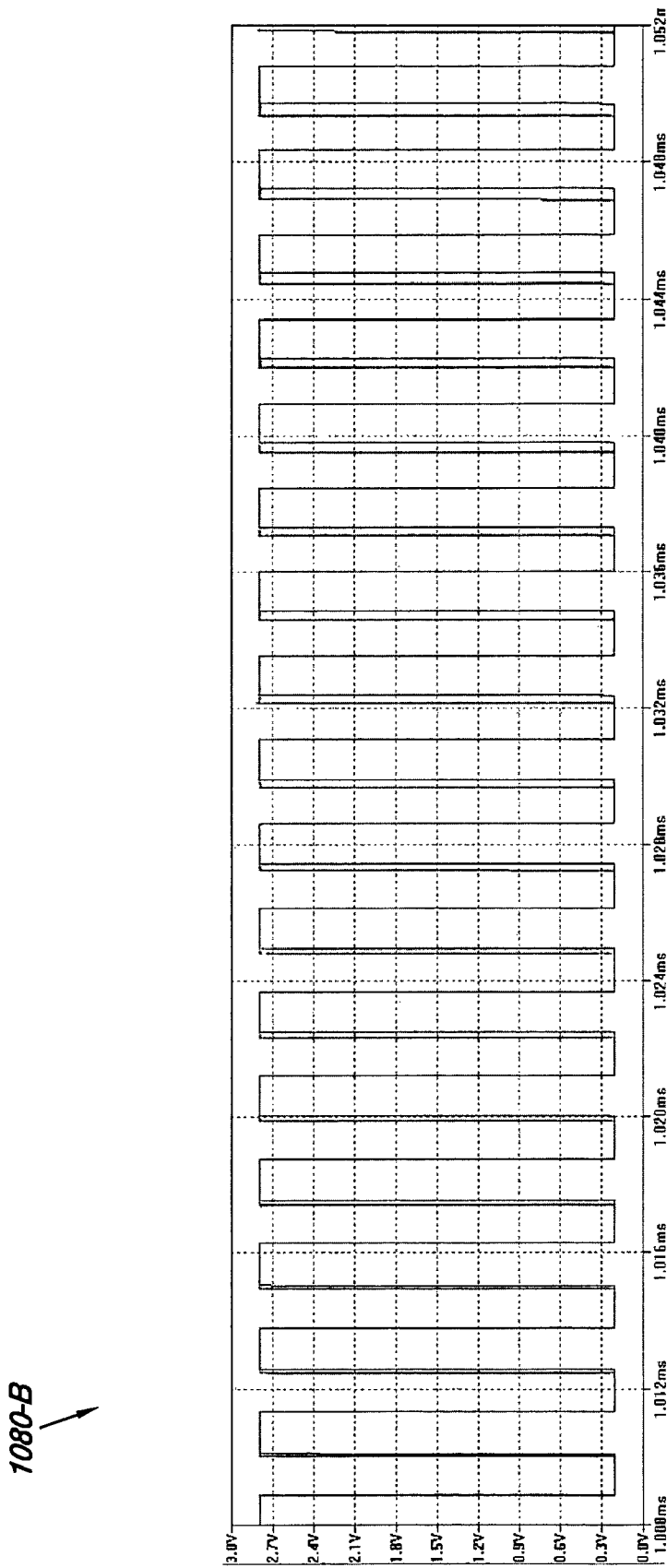
FIG. 10B illustrates a diagram of a portion of the signal illustrated in FIG. 7 after pulse-width modulation in accordance with one or more embodiments of the present disclosure.

FIG. 10B illustrates a diagram of a portion of the signal illustrated in FIG. 7 after pulse-width modulation in accordance with one or more embodiments of the present disclosure. The diagram 1080-B shows the result of pulse-width modulating the audio signal illustrated in FIG. 7 with a sawtooth wave, e.g., a sawtooth wave generated by the sawtooth wave generator 643 illustrated in FIG. 6. The pulse-width modulated signal illustrated in diagram 1080-B can be input to an amplitude modulation circuit, e.g., amplitude modulation circuit 624 in FIG. 6.

The diagram 1080-B is presented with a narrower scale than diagram 700 to provide additional detail on the signal image to illustrate the digital nature of the signal after pulse-with modulation. The voltage range of the signal illustrated in diagram 1080-B is approximately 0.25 volts-2.75 volts, or an approximately 2.5 volt range.

FIG. 11 illustrates a diagram of an amplitude and pulse-width modulated signal as output from a transmission coil in accordance with one or more embodiments of the present disclosure. The diagram 1180 can represent the output of inductive coil 410 in FIG. 4 according to an input equal to the signal illustrated in diagram 980 in FIG. 9.

Note that the voltage range of the signal is approximately ±2.5 volts, e.g., an approximately 5 volt range. Thus, a 5 volt range output was generated from a relatively low powered input having a voltage range of approximately 1 volt as described above in connection with FIG. 9.

According to some previous approaches that use amplitude modulation without pulse width modulation, a voltage range after pulse-width modulation can be approximately 0-2.8 volts while the voltage across the transmission coil can be greater than ±3 volts, e.g., greater than a common power supply voltage level for cochlear implants. Accordingly, some previous approaches included the use of additional circuitry to convert a provided power supply to a greater level, e.g., ±5 volts, as well as the inclusion of a number of amplifiers to raise the voltage to the appropriate level.

In contrast, one or more embodiments of the present disclosure can operate within a voltage range of a power supply that may be used with cochlear implants. For example, two 1.4 volt hearing aid type batteries may be used with one or more embodiments of the present disclosure to provide a 2.8 volt power supply.

As will be appreciated, the diagram 1180 appears to illustrate an analog signal, e.g., a transmission signal, in the aspect in which it is presented. As the details of the signal in diagram 1180 may be difficult to observe, a "zoomed in" image of the signal is provided in FIG. 12 in a narrower scale. Note, however, that while the signal in diagram 1180 includes aspects of an analog and a digital signal, the signal received by the implanted reception coil, e.g., coil 214 in FIGS. 2A and 2B, is an analog signal, which would appear analogous to the signal illustrated in diagram 880 in FIG. 8.

FIG. 12 illustrates a diagram of a portion of the signal illustrated in FIG. 11 in accordance with one or more embodiments of the present disclosure. The diagram 1280 provides additional detail on the signal image to illustrate both the digital and analog nature of the signal transmitted by the transmission coil.

CONCLUSION

The present disclosure includes methods, devices, and systems for cochlear implants. One method embodiment for cochlear implant signal processing includes processing a differential analog audio signal using amplitude modulation and pulse-width modulation. The method includes driving a transmission coil on an external unit of the cochlear implant with the pulse-width and amplitude modulated signal. The method also includes driving a reception coil on an internal unit of the cochlear implant with an output of the transmission coil.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and methods are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method for cochlear implant signal processing, comprising:
   processing a differential analog audio signal using amplitude modulation and pulse-width modulation;
   driving a transmission coil on an external unit of the cochlear implant with the pulse-width and amplitude modulated signal; and
   driving a reception coil on an internal unit of the cochlear implant with an output of the transmission coil.

2. The method of claim 1, wherein the method includes driving a tuned circuit including the transmission coil with the pulse-width and amplitude modulated signal such that the transmission coil resonates at a frequency approximately equal to a frequency of the first signal.

3. The method of claim 1, wherein the method includes driving an electrode with the reception coil according to the output of the transmission coil.

4. The method of claim 3, wherein driving the electrode includes outputting an analog amplitude modulated signal from the reception coil to the electrode.

5. The method of claim 1, wherein the method includes feeding the pulse-width and amplitude modulated signal back to set a direct current level for modulating the differential analog audio signal.

6. The method of claim 1, wherein the method includes receiving the differential analog audio signal from a microphone on the external unit of the cochlear implant.

7. The method of claim 1, wherein processing the differential analog audio signal using amplitude modulation and pulse-width modulation includes processing the differential analog audio signal to generate a reduced-carrier amplitude modulated signal, wherein the reduced-carrier amplitude modulated signal has a carrier level reduced below a carrier level associated with an amplitude modulator for the differential analog audio signal.

8. The method of claim 7, wherein the method includes delivering the reduced-carrier amplitude modulated signal directly to a cochlea associated with the cochlear implant.

9. An external signal processing unit of a cochlear implant, comprising:
   a microphone;
   a processor coupled to the microphone including an amplitude modulation circuit and a pulse-width modulation circuit, wherein the processor is configured to process a differential analog audio signal; and
   a tuned circuit coupled to the amplitude modulation circuit and to the pulse-width modulation circuit, wherein the tuned circuit is configured to transmit a signal corresponding to a pulse-width and amplitude modulated signal.

10. The external unit of claim 9, wherein the amplitude modulation circuit includes:
   an oscillator configured to generate a carrier signal; and
   an analog switch having inputs including:
      the differential analog audio signal; and
      the carrier signal;
   wherein the analog switch is configured to:
      modulate the carrier signal with the differential analog audio signal; and
      output the modulated signal to the pulse-width modulation circuit.

11. The external unit of claim 10, wherein the pulse-width modulation circuit includes a comparator with inputs including:
   an output of a sawtooth wave generator; and
   the output from the amplitude modulation circuit.

12. The external unit of claim 11, wherein an output of the pulse-width modulation circuit is fed back to mix with the differential analog audio signal input to the analog switch.

13. The external unit of claim 9, wherein the pulse-width modulation circuit includes at least two comparators, each with an input from a complimentary signal of the differential analog audio signal and an input from a sawtooth generator.

14. The external unit of claim 13, wherein the amplitude modulation circuit comprises a digital multiplexer with inputs from the at least two comparators and an output to the tuned circuit.

15. The external unit of claim 9, wherein the tuned circuit is tuned to a frequency approximately equal to a frequency of a carrier signal associated with the amplitude modulation circuit; and
   wherein the tuned circuit includes a capacitor, a transmission coil, and a resistor coupled in series.

16. The external unit of claim 9, wherein the external unit includes at least one battery configured to provide power to the amplitude modulation circuit and the pulse-width modulation circuit.

* * * * *